United States Patent [19]

Das

[11] 3,964,865

[45] June 22, 1976

[54] LYOPHILIZED HUMAN HEMOGLOBIN STANDARD FOR COLORIMETRIC DETERMINATION OF TOTAL HEMOGLOBIN

[75] Inventor: Manik L. Das, Crestwood, Mo.

[73] Assignee: Sigma Chemical Company, St. Louis, Mo.

[22] Filed: Jan. 30, 1975

[21] Appl. No.: 545,298

[52] U.S. Cl. .............................. 23/230 B; 252/408; 356/39; 356/42; 356/185; 424/7
[51] Int. Cl.² .................. G01N 21/20; G01N 33/16
[58] Field of Search ............ 23/230 B; 426/384, 385; 252/408; 424/7; 356/39, 42

[56] References Cited
OTHER PUBLICATIONS

Harvey A. Itano et al., Medicine, 35, 131 (Feb. 1956).
Todd–Sanford Clinical Diagnosis, I. Davidson et al., eds., 14th Edition, 139, W. B. Saunders, Phila., 1969.
Gradwohl's Clinical Laboratory Methods, Sam Frankel et al., eds., vol. I, 396–406, C. V. Mosby Co., Saint Louis, 1970.

*Primary Examiner*—Morris O. Wolk
*Assistant Examiner*—Sidney Marantz
*Attorney, Agent, or Firm*—Polster and Polster

[57] ABSTRACT

A preweighed vial of lyophilized methemoglobin (ferrihemoglobin) provides a simple, stable, reproducible standard for colorimetric determination of total hemoglobin concentration in whole blood by the cyanmethemoglobin method. Conversion of the standard and of hemoglobin in blood samples to cyanmethemoglobin is accomplished with Drabkin's solution reconstituted from a dry powder and having an added non-ionic surface active agent (Brij-35). Color intensity is measured at 540 m$\mu$.

11 Claims, No Drawings

LYOPHILIZED HUMAN HEMOGLOBIN STANDARD FOR COLORIMETRIC DETERMINATION OF TOTAL HEMOGLOBIN

BACKGROUND OF THE INVENTION

This invention relates to an improved hemoglobin standard and to an improved total hemoglobin assay procedure utilizing the standard.

Ever since the early investigations of hemoglobin by Hoppe-Seyler, Gowers, Hufner and others in the 19th century, the importance of hemoglobin has been recognized, and simple diagnostic tests for hemoglobin concentration have been sought. In vitro measurements of hemoglobin are today among the most frequently performed diagnostic procedures and are important in the detection and management of anemia and other diseases associated with abnormal hemoglobin levels. Unfortunately, even now when millions of hemoglobin determinations are run annually and the accuracy of these tests is relied upon in choosing what therapy, if any, is to be utilized, there is no generally accepted, simple, sensitive and reproducible method for determining hemoglobin. See Federal Register 39, 9217 (Mar. 8, 1974).

Hemoglobin is also widely used in various types of research. A homogeneous, stable hemoglobin preparation of known quantity is thus a highly desirable article of commerce, and a simple colorimetric hemoglobin determination method would be highly valuable in the commercial manufacture of purified hemoglobin.

Mammalian hemoglobin is a chromoprotein in which a soluble basic protein molecule (globin), consisting of four polypeptide chains of similar molecular weight held together by non-convalent forces, is conjugated to four colored ferrous protoporphyrin (heme) molecules. The heme component is the same in all mammalian hemoglobins, but the globin component differs from species to species, from individual to individual of the same species, and even within the same individual.

Hemoglobin is capable of forming a number of derivatives attributable to the reactivity of its heme part, all of which are commonly referred to collectively as hemoglobin. This nomenclature will be used hereinafter, with the name ferrohemoglobin used for the parent molecule. In the circulating blood, hemoglobin's "respiratory function" is due to the reversible reaction of ferrohemoglobin with molecular oxygen to form oxyhemoglobin. These two forms of hemoglobin, therefore, constitute the active forms of hemoglobin in the circulating blood. Ferrohemoglobin also reacts reversibly with carbon monoxide to form carboxyhemoglobin and irreversibly with hydrogen sulfide to form sulfhemoglobin. Oxidizing agents, such as certain drugs or ferricyanide, oxidize the ferrous iron of ferrohemoglobin to the ferric state to form methemoglobin (ferrihemoglobin). Methemoglobin is reducible to ferrohemoglobin by reducing agents such as hydrosulfite, but it is unable to unite with molecular oxygen or carbon monoxide. Methemoglobin does form further derivatives by uniting with a number of anions, such as azide, cyanide and fluoride. All the common hemoglobins except sulfhemoglobin are interconvertible.

Ferrohemoglobin and its derivatives exhibit characteristic absorptioin spectra in the visible region of light, which provide a means for distinguishing them from one another both qualitatively and quantitatively. Generally, the spectral properties of ferrohemoglobin and its derivatives are not dependent on the nature of their globin components.

A number of chlorimetric methods have been described in the literature for the determination of the total hemoglobin concentration in whole blood. These methods initially pretreat a blood sample with a reagent, or diluting fluid, which converts all the hemoglobin in the blood sample into a suitable derivative. The color intensity of the diluted blood sample is measured in a colorimeter which has been calibrated with an appropriate color standard, either artificial or physiological. The use of a photoelectric colorimeter, rather than visual methods, is necessary to provide the degree of precision required in clinical tests. Although artificial color standards are regarded as stable, the estimation of hemoglobin using them is considered unreliable, largely because the light absorption properties of the standards do not exactly correspond with the light absorption properties of the hemoglobin derivatives. Therefore, colorimetric methods require the use of physiological standards derived by treating blood samples of known hemoglobin concentrations with the appropriate diluting fluid.

To avoid the discrepancies in hemoglobin estimation that arise from the heterogeneity of hemoglobin in blood (caused both by the genetic differences in the globin components and by the differences in relative proportions of ferrohemoglobin and its various derivatives), and to achieve uniformity in hemoglobin determinations, the National Academy of Sciences-National Research Council, U.S.A. (NRC), and the International Committee for Standardization in Haematology (ICSH) have both recommended the universal adoption of a "uniform" cyanmethemoglobin method and standard solution for colorimetric determination of hemoglobin. In brief, the method initially treats 0.02 ml of a blood sample with 5.0 ml of a diluting fluid to convert the hemoglobin in the sample into the cyanmethemoglobin derivative. The diluting fluid is an alkaline solution which contains 200 milligrams of $K_3Fe(CN)_6$ and 50 milligrams of KCN per liter. Color intensity is determined at 540 m$\mu$ with a photoelectric colorimeter. The colorimeter is calibrated with a cyanmethemoglobin standard solution which is of known concentration and which meets certain required specifications. The standard is produced by treatment of hemolyzed human blood with the standard diluting fluid in accordance with the recommended uniform method. The assignment of a universally accepted hemoglobin concentration to the standard solution by absolute spectrophotometry is made possible by arbitrarily assigning a molecular weight to hemoglobin of 64,458 (on the basis of the established molecular weight of hemoglobin-A), and by fixing the millimolar extinction coefficient of cyanmethemoglobin at 44.0. Therefore, the concentration of hemoglobin in the standard (mg./100 ml.) is given by equation (a):

$$Hb \text{ conc. (mg/100 ml)} = \frac{OD_{540} \times 64,458}{44.0 \times 10} \quad (a)$$

$$= 146.49 \times OD_{540} \text{ (1 cm light path)}.$$

Since the dilution factor of the procedure is 251, the corresponding gram percent of hemoglobin in the undiluted sample is given by Equation (b):

$$\frac{251}{} \quad uz, 20/28 \ OD_{540}$$

-continued $$\text{Sample } Hb \text{ conc. (gm\%)} = \frac{OD_{540}}{1000} \times \frac{\times 64{,}458}{44.0 \times 10} \quad (b)$$

$$= 36.77 \times OD_{540} \text{ (1.0 cm light path)}.$$

The recommendations of these two groups and discussions of the recommendations are contained, for example, in Cannan, *Blood*, 13, 1101 (1958); Cannan, *Am. J. Clin. Pathol*, 44, 207 (1965); Standardization in Hematology (ed. G. Astaldi et al.) Fondazione Carlo Erba, Milan, Italy 1970; Eilers, *Am. J. Clin. Pathol.*, 47, 212 (1967); and Bibliotheca Haematologica, Vol 21 (ed. C. DeBoroviczeny), Basel/New York 1965.

The uniform cyanmethemoglobin method meets most of the requirements for a suitable colorimetric method. The diluting fluid converts to cyanmethemoglobin all forms of hemoglobin, except sulfhemoglobin, that are likely to be present in the circulation. Because the millimolar extinction coefficients of cyanmethemoglobin and sulfhemoglobin at 540 m$\mu$ are close, the presence of a small amount of sulfhemoglobin does not affect accuracy significantly.

The absorption curve of cyanmethemoglobin shows a flat maximum around 540 m$\mu$.

The diluting fluid may be prepared as a single reagent, and its pH and ionic strength do not influence the color intensity produced by the reaction, although they do determine the reaction time and the clarity of the final reaction mixture. A diluting fluid of low pH and ionic strength appears to favor both the rate of hemolysis and the rate of formation of cyanmethemoglobin, but is likely to cause turbidity in the final reaction mixture as a result of the partial solubility of plasma proteins and erythrocyte stromata, which require higher pH and ionic strength for solubilization. One diluting fluid in wide use is a low pH solution developed by Van Kampen and Zijlstra, which contains one hundred forty milligrams $KH_2PO_4$ and 0.5 milliliters Sterox SE per liter in addition to the $K_3Fe(CN)_6$ and KCN. The solution has a low pH of about 7.2 and the Sterox SE, a non-ionic surfactant, reduces turbidity to an acceptable level. A second widely used diluting fluid is based on a recipe by Drabkin and includes one gram of $NaHCO_3$ per liter in addition to the $K_3Fe(CN)_6$ and KCN, to maintain a relatively high pH of about 8.6. Both diluting fluids suffer from deterioration over a period of time. At low temperatures (refrigerator), the $K_3Fe(CN)_6$ and KCN tend to form $K_4Fe(CN)_6$ and KCNO, with an attendant fading of the yellow color of the solution. At room temperature the solutions are susceptible to contamination by microorganisms. The solutions are particularly likely to undergo changes due to temperature variations during shipping, even if they have been sterilized and are shipped in hard borosilicate glass containers. Weatherburn and Logan, *Clin. Chim. Acta.*, 9, 581 (1964) have suggested the preparation and distribution of a dry mixture of Drabkin's ingredients. The dry mixture is temperature insensitive and may be shipped without danger of decomposition. The Van Kampen-Zijlstra solution reacts faster with a sample but is not amenable to shipment as a dry mixture. Attempts to ship it as a concentrate have failed because of rapid decomposition.

The greatest problem with the NRC-ICSH recommended uniform cyanmethemoglobin colorimetric method lies in the standard solution required for calibrating the colorimeter. An approved cyanmethemoglobin standard solution is prepared from red cell hemolysate free from erythrocyte stromata, by diluting the hemolysate with the same diluting fluid which is to be used for treating blood samples. To assure that the standard solution is suitable, it must carry the seal of certification of competent authorities recognized by NCR-ICSH and must meet specifications with regard to its hemoglobin concentration, purity, and turbidity. Concentration, checked spectrophotometrically, should be between 59.77 and 79.69 mg. hemoglobin/100 ml. (OD(1 cm. path)=0.408–0.544), which is equivalent to between 15 and 20 gram percent hemoglobin in whole blood, diluted 1:251. The concentration must not change more than ±2% during the stated life of the standard. The purity of the standard is checked by inspecting the shape of its absorption curve between 450 and 700 m$\mu$ for consistency with a curve derived from a pure cyanmethemoglobin solution. Purity is also checked spectrophotometrically by determining the ratio of optical density at 540 m$\mu$ to optical density at 504 m$\mu$. This ratio should be between 1.58 and 1.62 because those standard solutions with the highest ratios (i.e. those in this range) appear to be the most stable. The turbidity of the standard is checked spectrophotometrically by measuring its $OD_{750}$ (1 cm. path), the value of which should be less than or equal to 0.002.

If stipulated criteria for purity and clarity were always met by carefully prepared cyanmethemoglobin standard solutions, and if meeting these criteria guaranteed the suitability of the cyanmethemoglobin standard for calibrating or recalibrating a colorimeter many days and miles removed from the time and place the tests were met, the NRC-ICSH recommendations for a uniform cyanmethemoglobin method would probably be widely accepted as a relatively simple, sensitive, and reliable method for determining total hemoglobin. However, the criteria are not always met and the stability of even the most carefully prepared standard solutions is open to serious question.

Some of the problems with meeting the criteria are set out, for example, in a paper by Moran entitled "Challenge to the Criteria" in Standardization in Hemotology (ed. G. Astaldi et al.) Fondazione Carlo Erba, Milan, Italy 1970. Briefly, although changes with time in the $OD_{540}/OD_{504}$ value of a particular standard solution probably indicate deterioration, the measured value of this ratio for any given freshly prepared standard rarely falls within the prescribed range. This is true whether the standard is prepared from crystalline hemoglobin preparations or from red cell hemolysate and in spite of the fact that freshly prepared cyanmethemoglobin standard solutions obtained from purified hemoglobin preparations consistently produce absorption curves that are characteristic of cyanmethemoglobin. The usefulness of the $OD_{750}$ measurement as an indication of turbidity has also been questioned by Moran and others.

Although the cyanmethemoglobin standard solution has sometimes been reported as stable in storage, if maintained in the dark under sterile conditions at 0°–4°C, there is considerable evidence that the stability of the solution is at best unpredictable, particularly during shipment. See, for example, Cannan, *Blood*, 13, 1101 (1958); Ressler et al. *J. Lab. & Clin. Med.*, 54, 304 (1959); and Von Klein-Wisenberg & Clotten, in Bibliotheca Haematologica, Vol. 21, pp. 79–95. These authors suggest that the instability is due to the microorganisms or to impurities in the standard, and that the solutions should be made more carefully, although they do not suggest exactly what care is necessary. The instability of the diluting fluid portion of the standard affects the optical density of the standard at 540 m$\mu$. More importantly, in an alkaline solution containing $K_3Fe(CN)_6$ the stability of the hemoglobin itself is doubtful. The lability of proteins in dilute solution, and in particular of human hemoglobin, has frequently been commented upon, for example by Cannan, supra, and by Itano in Advances in Protein Chemistry, Vol. 12 at 212, 222. Work by Riggs and Wolbach, J. Gen. Physiol., 39, 585, 600 (1956), and by Mirsky and Anson, J. Gen. Physiol., 19, 439 (1936), indicates the oxidation of the SH groups of hemoglobin in alkaline solutions of hemoglobin similar to the proposed standard, and therefore suggests that the cyanmethemoglobin standard solution is liable to undergo deterioration in storage due to intermolecular disulfide bond formation.

SUMMARY OF THE INVENTION

One of the objects of this invention is to provide a standard, for use in colorimetric determination of hemoglobin, which is highly reliable even after prolonged storage.

Another object is to provide such a standard which is easy to transport, store, and use.

Another object is to provide a test kit for colorimetric hemoglobin determinations which provides accurate results and which is easy to transport, store, and use.

Other objects will become apparent to those skilled in the art in light of the following description.

In accordance with one aspect of this invention, generally stated, a stable, reliable hemoglobin standard is provided in the form of a known quantity of dry, lyophilized methemoglobin (ferrihemoglobin) in a vacuum-sealed vial.

In accordance with another aspect of this invention, a kit is provided for the colorimetric determination of hemoglobin, which includes a preweighed, dry $K_3Fe(CN)_6/KCN$ reagent, a liquid surface active agent, and a preweighed, dry, stable hemoglobin standard. The standard is preferably the lyophilized methemoglobin standard of the present invention, although dry preparations of hemoglobins which have been indicated in the literature to be stable may be usable. Itano et al., Medicine, 35, 121 (1965), report that carbonmonoxyhemoglobin and ferrohemoglobin can be lyophilized and reconstituted with little change in their absorption spectra and activity. Itano et al further report that ferrihemoglobin (presumably in solution) is also stable if stored with oxygen excluded, but that its preparation requires more time and care than carbonmonoxyhemoglobin.

The lyophilized standard is easily prepared from a crude hemoglobin preparation by filtration through a 20–24 micron filter. During filtration, substantially all of the hemoglobin in the solution is oxidized to methemoglobin by the ambient air. The methemoglobin filtrate is then assayed and its concentration adjusted to a standardized value. Aliquots of the filtrate are lyophilized and vacuum-sealed. The resulting dry, preweighed powder is suitable for use as a primary standard for the colorimetric determination of hemoglobin. The dry standard is stable almost indefinitely in the dark at 4°C, and shows extended stability even at room temperature. It is easily converted to a cyanmethemoglobin standard solution by adding an aliquot of Drabkin's reagent prepared by reconstituting a dry, preweighed Drabkin's powder and, preferably, by addition of a small amount of non-ionic surface active agent. The measured $OD_{540}/OD_{504}$ ratio and the $OD_{750}$ value of the cyanmethemoglobin solution formed when the standard is reconstituted with Drabkin's reagent are consistently found to be 1.54±0.04 and 0.006±0.004, respectively. The reconstituted standard solution is highly suitable for use in the colorimetric estimation of hemoglobin in whole blood, since the mean measured $OD_{540}/OD_{504}$ and $OD_{750}$ values of blood samples pretreated with Drabkin's reagent are found to correspond to the mean measured values of the reconstituted cyanmethemoglobin standard solution.

DESCRIPTION OF THE PREFERRED EMBODIMENT

The following examples are the presently preferred method for producing a dry, stable lyophilized methemoglobin standard, the presently preferred reagent kit for colorimetric determination of hemoglobin, and the presently preferred method for determining hemoglobin colorimetrically in accordance with the present invention.

EXAMPLE 1

Preparation of hemoglobin standard.

A crude preparation of human hemoglobin is obtained by hemolysis of whole blood in accordance with standard procedure. A solution of the crude hemoglobin is filtered to remove denatured product. During filtration, more than 99% of the hemoglobin in the solution is oxidized to methemoglobin. Because the solution is acidic, little if any further denaturation occurs. The filtrate is assayed for hemoglobin and diluted to a predetermined methemoglobin concentration. Aliquots of the filtrate are placed in glass vials, which are placed in a standard lyophilizer where the methemoglobin is freeze-dried and the vials capped under vacuum. A further assay of selected vials provides a check on the quantity and purity of the lyophilized methemoglobin.

The vacuum-sealed lyophilized methemoglobin, when reconstituted with water (pH 5.8) yields a smooth absorption curve from 450 to 650 m$\mu$ which corresponds substantially identically to the published curve for methemoglobin (pH 7.0 to 7.4). When reconstituted with Drabkin's reagent, it yields a smooth absorption curve which corresponds substantially identically with the published curve for cyanmethemoglobin. On the basis of the absorption data in the visible region, the dry standard may be characterized as substantially pure methemoglobin. More importantly, because of the highly characteristic absorption curves of the reconstituted methemoglobin and cyanmethemoglobin solutions, the lyophilized methemoglobin is an ideal colorimetric standard.

EXAMPLE 2

Test Kit

A particularly convenient test kit containing all the reagents necessary for simple and reliable colorimetric determination of hemoglobin consists of the following reagents, which may be individually packaged and shipped as a unit in a cardboard container.

A. Hemoglobin Standard. A vacuum-sealed first vial contains 35.8 ± 0.6 mg. hemoglobin in the form of dry, lyophilized methemoglobin prepared in accordance with Example 1. The weight of hemoglobin is based on the standard NRC-ICSH molecular weight of hemoglobin (64,458) millimolar extinction coefficient of cyanmethemoglobin (44.0). The vial is sized to contain in excess of 50 ml, and is labeled with the assayed weight of hemoglobin in it.

The dry standard is preferably kept in the dark at 0°–4°C, e.g. in a refrigerator, as is the reconstituted cyanmethemoglobin standard solution. Table 1 shows optical density values of cyanmethemoglobin solutions freshly prepared by addition of 50 millimeters of Drabkin's solution to a vial of the dry standard which has been stored under refrigeration. Measurements were made using a Beckman DU spectrophotometer and cuvettes having a one centimeter light path.

TABLE 1

| Batch | Vial No. | Age of Dry Standard | DU $OD_{540}$ | DU $OD_{540}/OD_{504}$ | DU $OD_{750}$ |
|---|---|---|---|---|---|
| A | 1 | 3 days | .488 | 1.52 | .003 |
| A | 2 | 3 days | .482 | 1.52 | .004 |
| A | 3 | 3 days | .481 | 1.53 | .004 |
| A | 4 | 3 days | .485 | 1.52 | .005 |
| A | 5 | 3 days | .485 | 1.51 | .005 |
| A | 6 | 3 days | .486 | 1.52 | .004 |
| A | 7 | 3 days | .490 | 1.53 | .005 |
| A | 8 | 24 wks. | .492 | 1.53 | .008 |
| A | 9 | 24 wks. | .490 | 1.51 | .007 |
| A | 10 | 24 wks.* | .483 | 1.51 | .008 |
| A | 11 | 27 wks.** | .485 | 1.50 | .008 |
| A | 12 | 27 wks.*** | .464 | — | — |
| B | 13 | 33 wks. | .491 | 1.51 | .008 |
| B | 14 | 33 wks. | .484 | 1.52 | .005 |
| B | 15 | 33 wks. | .485 | 1.52 | .006 |
| B | 16 | 35 wks. | .484 | 1.51 | .006 |
| B | 17 | 36 wks. | .489 | 1.54 | .004 |
| B | 18 | 43 wks. | .490 | 1.53 | .006 |
| B | 19 | 69 wks. | .491 | 1.52 | .007 |
| B | 20 | 110 wks. | .494 | 1.53 | .009 |
| B | 21 | 110 wks. | .490 | 1.52 | .008 |
| B | 22 | 110 wks.* | .489 | 1.51 | .010 |
| B | 23 | 113 wks.** | .488 | 1.51 | .008 |
| B | 24 | 113 wks.*** | .468 | — | — |

*Vials 10 and 22 were kept for the last week of storage at 37°C.
**Vials 11 and 23 were kept for the last 3 weeks of storage at room temperature (about 23°C).
***Vials 12 and 24 were kept for the last month of storage at 37°C; $OD_{504}$ and $OD_{750}$ were not measured.

It thus appears that the dry standard is well able to withstand the rigors of shipment and, when stored in the dark at 0°–4°C, is stable for more than two years.

B. Drabkin's Reagent (Dry Mixture). A second vial contains 1.25 g. of a dry mixture of $NaHCO_3$, $K_3Fe(CN)_6$ and KCN in a weight ratio of 100:20:5. The reagent is stable for at least two years when stored in the dark. The optical density at 420 mµ of a freshly reconstituted Drabkin's solution, prepared as set out hereinbelow, was measured to be 0.590 (1 cm. light path) when made from a newly prepared Drabkin's powder. Seventy weeks later, a freshly reconstituted Drabkin's solution prepared from the same powder had an optical density of 0.570; 110 weeks later, a freshly reconstituted solution had an optical density of 0.565. As described in Example 3A., infra, these values are well within the range of usefulness of the reagent.

C. Non-ionic Surface-Active Agent. A third bottle contains 30.0% Brij-35 in an aqueous medium. The solution is stable at room temperature.

All three reagents making up this kit are relatively temperature insensitive and the kit is therefore easily and reliably transported.

EXAMPLE 3

Colorimetric Determination of Hemoglobin

The test kit of Example 2 is utilized for the colorimetric determination of total hemoglobin in a sample of human blood as follows.

A. Reconstitution of reagents

The hemoglobin standard (reagent A) vial is opened and to it is added precisely 50 ml. of Drabkin's reagent reconstituted as set out below. The vial is recapped, shaken to dissolve the standard, and allowed to stand for 40 minutes for complete conversion to cyanmethemoglobin. The reconstituted standard has a concentration equivalent to 18.0 ± 0.3 gram percent hemoglobin in whole blood diluted 1:251 in accordance with the standard NRC-ICSH procedure.

The reconstituted cyanmethemoglobin standard solution is stable for at least four to six months so long as the solution's sterility is maintained and so long as no visible fading of its color occurs. The stability of the reconstituted cyanmethemoglobin standard solution was tested by measuring optical density values of certain of the solutions set out in Table 1, after varying lengths of storage of the solution in the dark at 0°–4°C.

TABLE 2

| Solution (Vial) No. | Time After Reconstitution | DU $OD_{540}$ | DU $OD_{540}/OD_{504}$ | DU $OD_{750}$ |
|---|---|---|---|---|
| 1 | 23 wks. | .488 | 1.52 | .004 |
| 2 | 23 wks. | .480 | 1.52 | .004 |
| 3 | 23 wks | .480 | 1.52 | .004 |
| 4 | 23 wks. | .484 | 1.52 | .005 |
| 5 | 23 wks. | .485 | 1.51 | .004 |
| 6 | 23 wks. | .480 | 1.52 | .004 |
| 7 | 23 wks. | .488 | 1.52 | .006 |
| 13 | 76 wks. | .492 | 1.49 | .008 |
| 14 | 76 wks. | .479 | 1.52 | .004 |
| 15 | 76 wks. | .482 | 1.51 | .007 |
| 16 | 75 wks. | .460 | 1.44 | .006 |
| 17 | 33 wks. | .478 | 1.52 | .005 |
| 18 | 26 wks. | .489 | 1.51 | .007 |
| 18 | 66 wks. | .482 | 1.49 | .008 |

TABLE 2-continued

| Solution (Vial) No. | Time After Reconstitution | DU OD$_{540}$ | DU OD$_{540}$/OD$_{504}$ | DU OD$_{750}$ |
|---|---|---|---|---|
| 19 | 40 wks. | .478 | 1.51 | .006 |

The entire contents of the dry Drabkin's Reagent (Reagent B) vial is transferred to a one liter volumetric flask and the empty vial washed with distilled or deionized water. The washings are also transferred to the volumetric flask and additional water added with mixing until the reagent dissolves. The solution is then diluted to one liter. To this solution is added with mixing one-half ml. of the 30% Brij-35 solution (Reagent C). The reconstituted solution is stable for more than nine months if stored in a brown bottle of hard borosilicate glass at room temperature and maintained sterile. It must not be frozen. After seventy weeks, the first-mentioned reconstituted Drabkin's solution in Example 2B had an optical density at 420 m$\mu$ of 0.580 (1 cm. light path); after one hundred ten weeks its OD was 0.218, and it yielded hemoglobin readings which were up to 8% too high. Other reconstituted Drabkin's solutions showed similar stability, the least stable showing an OD$_{420}$ of .422 after more than 60 weeks of storage; this solution yielded hemoglobin readings which were accurate within 1%, or within the range of instrumental error. All of the solutions optically clear and showed negligible absorbance at 540 m$\mu$.

B. Preparation of calibration curve

A calibration curve for a particular colorimeter with a particular yellow-green filter is obtained by making a number of dilutions of the reconstituted cyanmethemoglobin standard with the reconstituted Drabkin's reagent. For example, six dilutions in the ratios of 6:0, 5:1, 4:2, 3:3, 2:4, and 0:6 (blank), representing 18, 15, 12, 9, 6, and 0 gram percent hemoglobin in whole blood, are sufficient. Optical density (or percent transmission) of each is then measured against the reconstituted Drabkin's reagent as blank and is plotted against concentration on suitable graph paper. If optical density is plotted on rectangular coordinates the result should be a straight line.

C. Specimen collection and preparation

Blood samples to be used for the determination of the total hemoglobin concentration should be collected from finger prick or heel stick (new born) and should be free flowing to prevent dilution with tissue fluid. If the blood sample is collected by venipuncture, care should be taken that it is not hemolyzed or partially clotted.

The materials which are known to cause interference in previous procedures by producing turbidity in the cyanmethemoglobin reaction mixture are erythrocyte stromata and abnormal plasma proteins that are derived from certain pathological blood samples. The employed diluting fluid containing Brij-35 avoids the problem of turbidity in the reaction mixture.

D. Test procedure

One test tube is marked TEST and a second test tube is marked BLANK. To each tube is added 5.0 ml. reconstituted Drabkin's reagent. To the tube marked TEST, 0.02 ml. of blood sample is transferred with a Sahli type pipette by placing the pipette tip at the bottom of the tube, and then rinsing the pipette three times with the Drabkin's reagent in the tube. Before the blood is added to the tube, excess blood on the outside of the pipette should be carefully wiped off. The contents of the tube marked TEST are mixed and the tube allowed to stand for 15 to 20 minutes at room temperature. The optical density (or percent transmission) of the mixture is then measured against the BLANK as reference. This value is then compared with the calibration curve to determine hemoglobin concentration in the blood sample.

It is believed that 12 to 17 gram percent is normal for males, and that 11 to 15 gram percent is normal for females, although, as noted previously, changes in hemoglobin levels may be more significant in many diagnoses than absolute values.

EXAMPLE 4

Statistical Evaluation of Procedure

The accuracy of the present method, using a reconstituted dry hemoglobin standard, has been found to be excellent when the method is utilized with widely differing blood samples. Table 3 shows results of hemoglobin determinations on identical samples made at 540 m$\mu$ with a Beckman DU spectrophotometer with one cm. cuvettes as compared with determinations made with a Coleman Jr. colorimeter (19 mm. light path) and a calibration curve prepared using the cyanmethemoglobin standard solution prepared in accordance with Example 3 from the lyophilized methemoglobin standard of Example 1. Table 3 also shows the close correspondence between OD$_{750}$ values and OD$_{540}$/OD$_{504}$ ratios of typical blood samples and those of the reconstituted standard.

TABLE 3

| Sex | Sample No. | DU OD$_{540}$ | DU OD$_{504}$/OD$_{540}$ | DU OD$_{750}$ | Coleman OD$_{540}$ | DU Estimated Hemoglobin (Gm%)* | Coleman Estimated Hemoglobin (Gm%)** |
|---|---|---|---|---|---|---|---|
| M | 1 | .425 | 1.545 | .004 | .632 | 15.63 | 15.55 |
|   | 2 | .397 | 1.521 | .004 | .590 | 14.60 | 14.52 |
|   | 3 | .409 | 1.555 | .005 | .620 | 15.04 | 15.20 |
|   | 4 | .347 | 1.535 | .005 | .520 | 12.76 | 12.80 |
|   | 5 | .501 | 1.556 | .004 | .739 | 18.42 | 18.20 |
|   | 6 | .464 | 1.550 | .005 | .590 | 17.00 | 16.90 |
|   | 7 | .497 | 1.530 | .004 | .741 | 18.27 | 18.24 |
|   | 8 | .507 | 1.504 | .004 | .770 | 18.64 | 18.80 |
|   | 9 | .407 | 1.542 | .004 | .610 | 14.97 | 15.00 |
|   | 10 | .425 | 1.534 | .004 | .631 | 15.63 | 15.53 |
|   | 11 | .407 | 1.542 | .003 | .610 | 14.97 | 15.10 |
| F | 1 | .384 | 1.548 | .004 | .579 | 14.12 | 14.25 |

TABLE 3-continued

| Sex | Sample No. | DU OD$_{540}$ | DU OD$_{504}$/ OD$_{540}$ | DU OD$_{750}$ | Coleman OD$_{540}$ | DU Estimated Hemoglobin (Gm%)* | Coleman Estimated Hemoglobin (Gm%)** |
|---|---|---|---|---|---|---|---|
| | 2 | .332 | 1.537 | .005 | .500 | 12.21 | 12.30 |
| | 3 | .315 | 1.529 | .006 | .478 | 11.58 | 11.60 |
| | 4 | .369 | 1.563 | .005 | .550 | 13.57 | 13.53 |
| | 5 | .329 | 1.537 | .004 | .499 | 12.10 | 12.20 |
| | 6 | .356 | 1.548 | .003 | .540 | 13.10 | 13.25 |
| | 7 | .407 | 1.553 | .003 | .613 | 14.97 | 15.00 |
| | 8 | .357 | 1.513 | .004 | .534 | 13.13 | 13.14 |
| | 9 | .398 | 1.543 | .003 | .598 | 14.63 | 14.72 |
| | 10 | .428 | 1.550 | .003 | .640 | 15.74 | 15.75 |
| | 11 | .462 | 1.540 | .004 | .691 | 16.99 | 17.00 |

*Estimated by using the equation (b): Hemoglobin Concentration (Gm%) = 36.77 × OD$_{540}$ (1 cm. path).
**Estimated by using the Coleman calibration curve.

A second series of fifteen whole blood specimens having hemoglobin concentrations of from 7.76 to 17.80 gm% (mean value: 14.47 gm%) was analyzed on the same two instruments. The greatest difference between the concentrations found for any specimen was 2%. The correlation coefficient was calculated to be 0.9986.

Reproducibility studies were performed on diluted and undiluted whole blood specimens with total hemoglobin concentration of 5.26, 8.04, and 16.1 gm/100 ml. Each specimen was analyzed with a Coleman Jr. (19 mm. light path) colorimeter on ten separate occasions. Calculated values of standard deviation were found to be 0.02, 0.08, and 0.06 gm/100 ml., respectively. Calculated values of coefficient of variation were 0.438%, 0.999%, and 0.380%, respectively.

As shown in Table 4, other photoelectric colorimeters using calibration curves prepared in accordance with Example 3B also provide close agreement with spectrophotometrically estimated hemoglobin values.

TABLE 4

| Sample No. | Spectrophotometrically Estimated Values of Hemoglobin Concentration, in Gm% | Colorimetrically Estimated Values Hemoglobin Concentration, in Gm% | | |
|---|---|---|---|---|
| | | Spectronic 20 set at 540 mμ | Klett, Filter No. 58 | Coleman Jr. set at 540 mμ |
| 1 | 17.1 | 16.8 | 17.0 | 16.9 |
| 2 | 20.0 | 19.9 | 19.4 | 19.4 |
| 3 | 17.7 | 17.7 | 17.5 | 17.5 |
| 4 | 17.6 | 17.7 | 17.5 | 17.4 |
| 5 | 11.7 | 11.6 | 12.0 | 11.8 |
| 6 | 15.8 | 15.7 | 15.5 | 15.6 |
| 7 | 17.4 | 17.1 | 17.0 | 17.1 |
| 8 | 14.7 | 14.7 | 14.7 | 14.7 |

The foregoing examples are merely illustrative, as numerous variations in the invention within the scope of the appended claims will occur to those skilled in the art.

I claim:

1. A stable reagent suitable for conversion in solution to a cyanmethemoglobin standard for use in a colorimetric method of determining total hemoglobin in a sample of human blood by converting the hemoglobin in solution to cyanmethemoglobin and comparing the resultant color with the cyanmethemoglobin standard, said reagent comprising a vacuum-sealed container containing a known quantity of dry, stable lyophilized methemoglobin derived from human blood.

2. A method for preparing lyophilized methemoglobin comprising filtering an acid solution of crude hemoglobin in an oxygen-containing atmosphere to remove denatured protein and to oxidize hemoglobin to methemoglobin, and thereafter freeze-drying the filtrate.

3. The method of claim 2 wherein said acid solution comprises hemolyzed blood.

4. The method of claim 2 wherein said lyophilized methemoglobin is prepared as a standard, said method including, between said filtering step and said freeze-drying step, a step of putting aliquots of filtrate into sealable vials.

5. In a method of colorimetrically determining total hemoglobin in a sample solution wherein the hemoglobin is converted in solution to a methemoglobin derivative and the color of the resultant solution is compared with the color produced by a standard solution of the same methemoglobin derivative, the improvement wherein said standard solution is prepared from a known quantity of lyophilized methemoglobin.

6. The improvement of claim 5 wherein said methemoglobin derivative is cyanmethemoglobin.

7. The improvement of claim 6 wherein the conversion of hemoglobin in said sample solution to cyanmethemoglobin is accomplished by addition of a solution prepared from a dry mixture comprising about five parts potassium cyanide, 20 parts potassium ferricyanide, and salt to maintain alkalinity of the reconstituted mixture.

8. The improvement of claim 6 wherein the conversion of hemoglobin in said sample solution to cyanmethemoglobin is accomplished by addition of a Drabkin's solution and a sufficient amount of a surfactant to inhibit turbidity caused by abnormal plasma proteins, by lipids and by erythrocyte stromata.

9. The improvement of claim 8 wherein said Drabkin's solution is prepared from a known quantity of a dry mixture comprising about five parts potassium cyanide, 20 parts potassium ferricyanide, and a salt to maintain alkalinity of the reconstituted mixture.

10. The improvement of claim 9 wherein the surfactant is an aqueous solution of a polyoxyethylene ether of a fatty alcohol.

11. In a method of colorimetrically determining total hemoglobin in a sample solution wherein the hemoglobin is converted in solution to cyanmethemoglobin and the color of the resultant solution is compared with a standard, the improvement wherein conversion of the hemoglobin in the sample to cyanmethemoglobin is accomplished by a reagent prepared from a non-ionic surface active agent and from a dry mixture comprising about five parts potassium cyanide, twenty parts potassium ferricyanide, and about one hundred parts of a salt to maintain a high ionic strength in the reconstituted reagent, said reconstituted reagent having a pH between about 8 and about 9; and wherein said standard is a solution prepared from: a known quantity of a dry, stable hemoglobin derivative; a non-ionic surface active agent; and a dry mixture comprising about five parts potassium cyanide, 20 parts ferricyanide, and about 100 parts of a salt to maintain a high ionic strength in the reconstituted standard, said reconstituted standard having a pH between about 8 and about 9.

* * * * *

UNITED STATES PATENT OFFICE
CERTIFICATE OF CORRECTION

Patent No. 3,964,865          Dated June 22, 1976

Inventor(s)          Manik L. Das

It is certified that error appears in the above-identified patent and that said Letters Patent are hereby corrected as shown below:

Col. 1, line 35, "non-convalent" should be "non-covalent".

Col. 2, line 3, "chlorimetric" should be "colorimetric".

Col. 5, line 49, "(1965)" should be "(1956)".

Col. 9, line 30, "solutions optically" should be "solutions remained optically".

Signed and Sealed this

Fifth Day of October 1976

[SEAL]

Attest:

RUTH C. MASON
Attesting Officer

C. MARSHALL DANN
Commissioner of Patents and Trademarks